United States Patent
Garel et al.

(10) Patent No.: US 12,152,002 B2
(45) Date of Patent: Nov. 26, 2024

(54) METHOD FOR THE TREATMENT OF A COMPOSITION COMPRISING NATURAL VANILLIN

(71) Applicant: SPECIALTY OPERATIONS FRANCE, Lyons (FR)

(72) Inventors: Laurent Garel, Lyons (FR); Rachid Djillali, Lyons (FR)

(73) Assignee: SPECIALTY OPERATIONS FRANCE, Lyons (FR)

( * ) Notice: Subject to any disclaimer, the term of this patent is extended or adjusted under 35 U.S.C. 154(b) by 453 days.

(21) Appl. No.: 17/627,153

(22) PCT Filed: Jul. 30, 2020

(86) PCT No.: PCT/EP2020/071489
§ 371 (c)(1),
(2) Date: Jan. 14, 2022

(87) PCT Pub. No.: WO2021/019005
PCT Pub. Date: Feb. 4, 2021

(65) Prior Publication Data
US 2023/0183159 A1    Jun. 15, 2023

(30) Foreign Application Priority Data
Jul. 30, 2019  (FR) ...................... 1908644

(51) Int. Cl.
*C07C 45/78*      (2006.01)

(52) U.S. Cl.
CPC .................. *C07C 45/78* (2013.01)

(58) Field of Classification Search
CPC .................................................. C07C 45/78
See application file for complete search history.

(56) References Cited

U.S. PATENT DOCUMENTS

| | | |
|---|---|---|
| 2,745,796 A | 5/1956 | Toppel |
| 6,362,378 B1 | 3/2002 | Jacquot et al. |
| 2014/0316165 A1 | 10/2014 | Vibert et al. |
| 2016/0039732 A1 | 2/2016 | Gayet et al. |
| 2019/0389792 A1 | 12/2019 | Vibert et al. |

FOREIGN PATENT DOCUMENTS

| | | |
|---|---|---|
| CN | 101165038 A | 4/2008 |
| DE | 1132113 B | 6/1962 |
| EP | 0885968 A1 | 12/1998 |
| EP | 2810564 A1 | 12/2012 |
| EP | 2791098 A1 | 10/2014 |
| FR | 2765870 A1 | 1/1999 |
| WO | 2014114590 A1 | 7/2014 |
| WO | 2018146210 A1 | 8/2018 |

OTHER PUBLICATIONS

Azadbkht, Preparation of lignin from wood dust as vanillin source and comparison of different extraction method, International Journal of Biology and Biotechnology, 2004, 535-537, vol. 1.

Avelino Corma, A General Method for the Preparation of Ethers Using Water-Resistant Solid Lewis Acids, Angew. Chem. Int. Ed., 2007, pp. 298-300, vol. 46.

Suhas Shinde, Cascade Reductive Etherification of Bioderived Aldehydes over Zr-Based Catalysts, Chemsuschem, 2017, pp. 4090-4101, vol. 10.

*Primary Examiner* — Sikarl A Witherspoon
(74) *Attorney, Agent, or Firm* — Osha Bergman Watanabe & Burton LLP

(57) ABSTRACT

The present invention relates to a process for treating a composition comprising natural vanillin by separating a compound of formula (I).

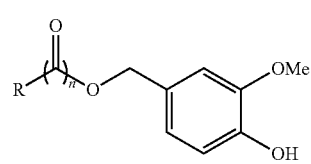

Formula (I)

18 Claims, No Drawings

METHOD FOR THE TREATMENT OF A COMPOSITION COMPRISING NATURAL VANILLIN

This application is a U.S. national stage entry under 35 U.S.C. § 371 of international patent application No. PCT/EP2020/071489 filed on Jul. 30, 2020, which claims priority to French patent application No. 1908644, filed on Jul. 30, 2019, the whole content of this application being explicitly incorporated herein by reference.

FIELD OF THE INVENTION

The present invention relates to a process for treating a composition comprising natural vanillin by separating a compound of formula (I).

PRIOR ART

Vanillin, or 4-hydroxy-3-methoxybenzaldehyde, may be obtained by various methods known to a person skilled in the art, in particular by the following three routes:
 A "natural" route based on a biotechnological process comprising in particular the culturing of a microorganism capable of enabling the bioconversion of a fermentation substrate into vanillin. Such a process in which the fermentation substrate is ferulic acid is in particular known from application EP 0 885 968. The ferulic acid used may be of several origins, in particular derived from rice bran or corn bran. These processes result in the preparation of a vanillin termed "natural vanillin".
 A "synthetic" route comprising conventional chemical reactions starting from guaiacol that does not involve a microorganism. This process results in the preparation of a vanillin termed synthetic vanillin.

Finally, vanillin may also be prepared according to a route described as "bio-based" in which the vanillin results from lignin; mention may in particular be made of the documents U.S. Pat. No. 2,745,796, DE 1132113 and the paper entitled "Preparation of lignin from wood dust as vanillin source and comparison of different extraction methods" by Azadbakht et al. in International Journal of Biology and Biotechnology, 2004, Vol. 1, No. 4, pp 535-537, or from eugenol.

When the "natural route" is used for the industrial production of vanillin, several side reactions may occur leading to the formation of numerous by-products which may affect the organoleptic properties of the natural vanillin. These by-products are also capable of reacting with, in particular, the vanillin. As a result, the purification yield of natural vanillin and also the overall yield of natural vanillin production are reduced. The organoleptic properties of the natural vanillin are also liable to be degraded.

In addition, the natural vanillin may be purified. For example, document WO 2018/146210 describes a process for purifying natural vanillin comprising at least one step of stripping a liquid stream comprising natural vanillin with an entraining gas and/or a vaporized liquid. Although this process makes it possible to purify the natural vanillin satisfactorily, the vanillyl alcohol is not removed satisfactorily.

The present invention aims to provide an effective solution for preventing side reactions with natural vanillin so as to improve the overall yield of the purification of natural vanillin, while maintaining, or even improving, its organoleptic properties.

BRIEF DESCRIPTION

Thus, a first subject of the present invention relates to a process for treating a composition (C) resulting from a process for producing natural vanillin comprising natural vanillin and vanillyl alcohol, comprising:
 a step (i) of forming a compound of formula (I) from vanillyl alcohol:

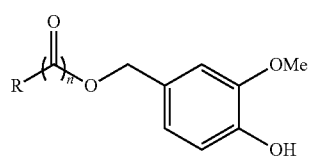

Formule (I)

wherein n is equal to 0 or 1, and R is chosen from a linear or branched, saturated or unsaturated alkyl group, optionally substituted with at least one hydroxyl, alkoxy or amine group, or R is a group of formula —(W—O)$_m$—X, wherein W is a linear or branched alkyl chain comprising from 1 to 4 carbon atoms and the average molecular weight of the —(W—O)$_m$— group is between 200 and 3000 g/mol and X is chosen from H and a unit of formula (II)

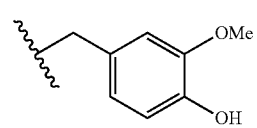

Formule (II)

wherein step (i) is carried out in the presence of natural vanillin and enables the formation of a composition (C1) or (C2);
 a step (ii) of recovering natural vanillin and/or a step of recovering a compound of formula (I), that are present in composition (C1) or (C2).

Another aspect relates to a process for purifying a composition comprising natural vanillin and vanillyl alcohol by separating a compound of formula (I).

The present invention also relates to a process for preparing a compound of formula (I) in the presence of natural vanillin.

Finally, the present invention relates to the use of a natural vanillin composition as a flavoring in the human and animal nutrition field, in pharmacy, and as a fragrance in the cosmetics, perfumery and detergency industries.

DETAILED DESCRIPTION

In the context of the present invention, and unless otherwise indicated, the expression "between . . . and . . . " includes the limits. Unless otherwise indicated, the percentages and ppm are percentages and ppm by weight.

In the context of the present invention, and unless otherwise indicated, the term "ppm" means "parts per million". This unit represents a fraction by weight: 1 ppm=1 mg/kg.

In the context of the present invention, and unless indicated otherwise, the expression "natural vanillin" may denote a flavoring substance according to Article 9.2c) of the Regulation EC 1334/2008, that is to say a flavoring substance obtained by physical, enzymatic or microbiological processes from materials of plant, animal or microbiological origin taken as they are or after conversion thereof for human consumption by one or more of the conventional processes for the preparation of foodstuffs. A natural flavoring substance corresponds to a substance which is naturally present and has been identified in nature. The definitions given by the regulations in force in other countries or regions may also be applied. Preferably, the term "natural vanillin" according to the present invention denotes vanillin obtained by a biotechnological process. According to another alternative, the term "natural vanillin" denotes vanillin obtained by a microbiological process, in particular comprising the culturing of a microorganism capable of enabling the conversion of a fermentation substrate into vanillin. According to the invention, the microorganism may be wild or be genetically modified, in particular in order to improve the performance, for example to improve the yield of vanillin, to limit or prevent the formation of by-products or else to increase the productivity. Very preferentially, it is a process for the fermentation of ferulic acid, as described in patent application EP 0 885 968. The ferulic acid may be of any origin, in particular derived from rice bran, beet pulp, wheat bran, bagasse, sugarcane or corn, in particular corn bran or corn fibers, in particular from starch factories or nixtamalization units.

In the context of the present invention, the term "alkyl" represents a linear or branched, saturated or unsaturated chain. Preferably, an alkyl group comprises from 1 to 10 carbon atoms, preferentially from 1 to 8 carbon atoms, and more preferentially still from 1 to 6 carbon atoms. An alkyl group may preferably be chosen from the group consisting of methyl, ethyl, propyl, isopropyl, n-butyl, s-butyl and tert-butyl. According to one particular aspect, the alkyl group may be substituted with at least one hydroxyl group. For example, the alkyl group substituted with at least one hydroxyl group may be —$CH_2$—CH(OH)—$CH_2$—OH.

Thus, a first subject of the present invention relates to a process for treating a composition (C) resulting from a process for producing natural vanillin comprising natural vanillin and vanillyl alcohol, said treatment process comprising:

a step (i) of forming a composition C1 comprising natural vanillin and a compound of formula (I) from said vanillyl alcohol present in composition (C):

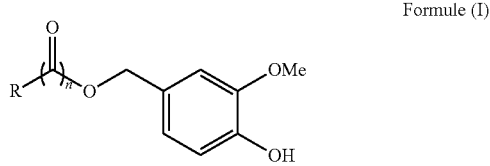

Formule (I)

wherein n is equal to 0 or 1, and R is chosen from a linear or branched, saturated or unsaturated alkyl group, optionally substituted with at least one hydroxyl, alkoxy or amine group, or a group of formula —(W—O)$_m$—X, wherein W is a linear or branched alkyl chain comprising from 1 to 4 carbon atoms and the average molecular weight of the —(W—O)$_m$— group is between 200 and 3000 g/mol and X is chosen from H and a unit of formula (II)

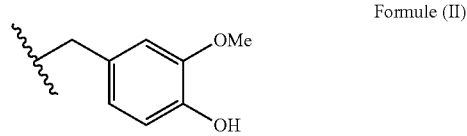

Formule (II)

a step (ii) of recovering natural vanillin and/or a step of recovering a compound of formula (I), that are present in composition (C1) or (C2). Preferably, n is equal to 0 and/or R is a butyl group.

Thus, the invention relates in particular to a process for treating a composition (C) comprising natural vanillin and vanillyl alcohol in which—composition (C) results from a process for producing natural vanillin—vanillyl alcohol is converted into the compound of formula I above, and in which a natural vanilla composition is purified.

According to the present invention, the weight concentration of natural vanillin in composition (C) is between 0.50% and 99%, preferably between 0.50% and 60%, preferentially between 5% and 40% and even more preferentially between 10% and 35% relative to the weight of the natural vanillin composition resulting from a process for producing natural vanillin.

According to the present invention, the composition (C) resulting from a process for producing natural vanillin comprises vanillyl alcohol. Generally, the weight concentration of vanillyl alcohol is between 0.1% and 5%, preferentially between 0.5% and 4% and even more preferentially between 1% and 2.5% relative to the weight of the natural vanillin composition (C) resulting from a process for producing natural vanillin.

According to the present invention, composition (C) may also comprise at least one compound chosen from vanillic acid, acetovanillone, guaiacol and vinyl guaiacol. Preferably, when composition (C) comprises acetovanillone, guaiacol is also present.

The present invention may further comprise a preliminary step of fermentation of a substrate, preferably ferulic acid, for the production of a composition resulting from a process for producing natural vanillin comprising vanillyl alcohol. The fermentation may be carried out as indicated in document EP 0 885 968. Fermentation is generally carried out in an aqueous medium. Composition (C) may be obtained from the fermentation medium or after treatment of the aqueous medium directly obtained at the end of the fermentation, making it possible in particular to remove the fermentation biomass.

Composition (C) used according to the treatment process of the present invention is generally obtained at the end of the fermentation step and optionally of the treatment of the aqueous medium directly obtained at the end of the fermentation.

Composition (C) may be in aqueous solution, or in a water/solvent mixture, preferably a water/organic solvent mixture. The organic solvent is generally a food solvent, in particular a solvent registered on the FEMA GRAS list. By way of example, mention may be made of ethanol, isopropanol, butanol, isobutyl alcohol, glycols and acetates, such as ethyl acetate and propyl acetate.

Step (i):

According to the present invention, step (i) is a step of forming a compound of formula (I) according to the following formula:

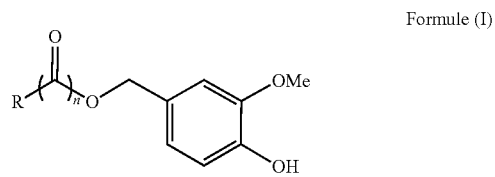

Formule (I)

wherein n is equal to 0 or 1, and R is chosen from a linear or branched, saturated or unsaturated alkyl group, optionally substituted with at least one hydroxyl, alkoxy or amine group, or a group of formula —(W—O)$_m$—X, wherein W is a linear or branched alkyl chain comprising from 1 to 4 carbon atoms and the average molecular weight of the —(W—O)$_m$— group is between 200 and 3000 g/mol and X is chosen from H and a unit of formula (II)

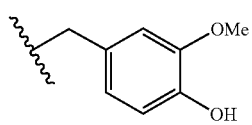

Formule (II)

In general, the average molecular weight of the —(W—O)$_m$— group is between 200 and 3000 g/mol, preferably greater than or equal to 300 g/mol, more preferentially greater than or equal to 350 g/mol. The average molecular weight of the —(W—O)$_m$— group is generally less than or equal to 2000 g/mol, preferably less than or equal to 1500 g/mol. The average molecular weight of the —(W—O)$_m$— group may be 400 g/mol or 600 g/mol.

According to a preferred aspect, step (i) is a step of forming a compound of formula (Ia) according to the following formula:

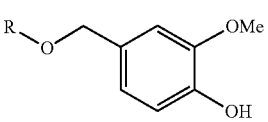

Formule (Ia)

wherein R is chosen from a linear or branched, saturated or unsaturated alkyl group, optionally substituted with at least one hydroxyl, alkoxy or amine group, or a group of formula —(W—O)$_m$—X, wherein W is a linear or branched alkyl chain comprising from 1 to 4 carbon atoms and the average molecular weight of the —(W—O)$_m$— group is between 200 and 3000 g/mol and X is chosen from H and a unit of formula (II)

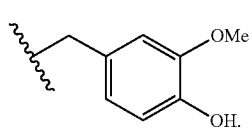

Formule (II)

According to another preferred aspect, step (i) is a step of forming a compound of formula (Ib) according to the following formula:

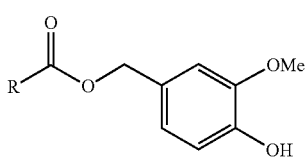

Formule (Ib)

wherein R is chosen from a linear or branched, saturated or unsaturated alkyl group, optionally substituted with at least one hydroxyl, alkoxy or amine group, or a group of formula —(W—O)$_m$—X, wherein W is a linear or branched alkyl chain comprising from 1 to 4 carbon atoms and the average molecular weight of the —(W—O)$_m$— group is between 200 and 3000 g/mol and X is chosen from H and a unit of formula (II)

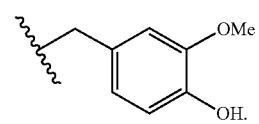

Formule (II)

According to the present invention, the group R is preferentially chosen from ethyl, n-butyl, n-propyl, i-propyl, i-butyl, optionally substituted with a hydroxyl group. Advantageously, the group R may be chosen from ethyl, n-butyl, OH—CH$_2$—CH$_2$—, OH—CH$_2$—CH(CH$_3$)—. In one variant, the group R is chosen from the above groups further comprising —CH$_2$—CH(OH)—CH$_2$—OH.

According to a preferred aspect, the compound of formula (Ia) is chosen from the group consisting of the compounds of formulae A to D:

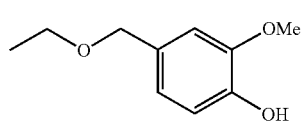

Formule (A)

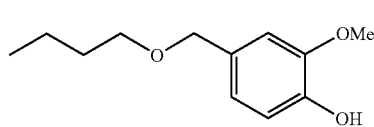

Formule (B)

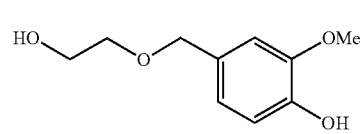

Formule (C)

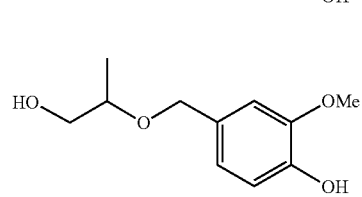

Formule (D)

According to a preferred aspect, the compound of formula (Ib) is chosen from the group consisting of the compounds of formulae E to H:

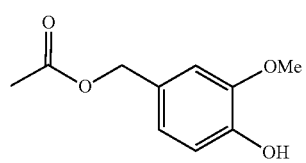

Formule (E)

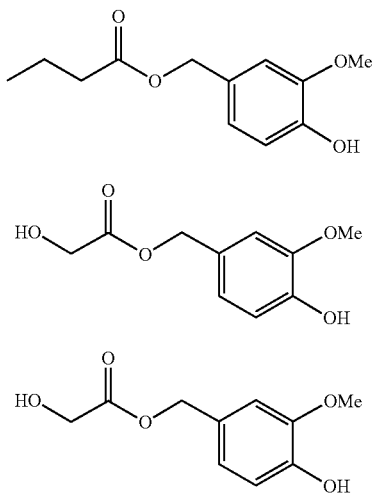

Formule (F)

Formule (G)

Formule (H)

According to the present invention, step (i) is an etherification or esterification reaction of the vanillyl alcohol present in composition (C). The etherification or esterification reaction is carried out in the presence of natural vanillin.

Advantageously, the etherification or esterification reaction is selective with respect to vanillyl alcohol. The etherification or esterification reaction is advantageously carried out without degradation of the natural vanillin. In particular, less than 10% by weight of the natural vanillin present in composition (C) is degraded, preferably less than 5%, more preferentially less than 1%, even more preferentially less than 0.1%. The amount of natural vanillin degraded may be calculated according to the following formula: (amount of natural vanillin initially in composition (C)—amount of natural vanillin remaining after step (i))/(amount of natural vanillin initially in composition (C)).

According to the present invention, the etherification or esterification reaction is carried out in the presence of a compound chosen from the group consisting of ROH, RCOOH, and HO—(W—O)$_m$—H, wherein R is chosen from a linear or branched, saturated or unsaturated alkyl group, optionally substituted with at least one hydroxyl, alkoxy or amine group and W is a linear or branched alkyl chain comprising from 1 to 4 carbon atoms and the average molecular weight of the HO—(WO)$_m$—H compound is between 200 and 3000 g/mol.

For example, the etherification reaction may comprise bringing the vanillyl alcohol present in composition (C) into contact with a compound of formula ROH, R being defined above. In particular, the esterification reaction may comprise bringing the vanillyl alcohol into contact with a compound of formula RCOOH, R being as defined above.

Advantageously, the primary alcohol group of the vanillyl alcohol reacts selectively with the compound of formula ROH or RCOOH in order to form the corresponding ether or ester of formula (I).

Thus, the invention relates in particular to a process for treating a composition (C) in which a composition C1 is formed, composition (C) comprising natural vanillin and vanillyl alcohol, said treatment process comprising:
  a step (i) wherein composition (C) is brought into contact with a compound of formula ROH or RCOOH, R having the definition above, in order to form a compound of formula (I) as defined previously and in order to obtain composition (C1), said composition (C1) comprising the compound of formula (I) and/or natural vanillin, and
  a step (ii) of recovering and/or purifying a natural vanillin composition and/or a compound of formula (I) present in the composition of formula (I).

Preferably, the treatment process according to the invention is a process in which step (i) is an etherification reaction carried out in the presence of a compound of formula ROH, R being a butyl group, and in which step (ii) is a step of recovering natural vanillin and/or of recovering a compound of formula (I) having n=0 and R being a butyl group.

In general, the average molecular weight of the HO—(W—O)$_m$—H compound is between 200 and 3000 g/mol, preferably greater than or equal to 300 g/mol, more preferentially greater than or equal to 350 g/mol. The average molecular weight of the HO—(W—O)$_m$—H group is generally less than or equal to 2000 g/mol, preferably less than or equal to 1500 g/mol. The average molecular weight of the HO—(W—O)$_m$—H group may be 400 g/mol or 600 g/mol.

According to one particular aspect, the etherification or esterification reaction is carried out in the presence of a compound which can be used in the agrifood industry.

According to the present invention, the reaction is carried out in the presence of an acid. The acid may be a strong acid. Preferably, the acid is chosen from the group consisting of HCl, $H_2SO_4$, para-toluenesulfonic acid (p-TsOH). The acid may also be a Lewis acid. Advantageously, sulfuric acid makes it possible to avoid the chlorination reaction of vanillin which may be observed with HCl.

According to the present invention, the reaction may be carried out in the presence of a mineral compound that is in solid form and displays acidic properties, such as a zeolite, in particular titanosilicalite, silicalite or oxides of silica, aluminum, titanium or zirconium. In particular, the reaction may be carried out in the presence of the zeolites described in the document *Angew. Chem. Int. Ed.* 2007, 46, 298-300.

The reaction may also be carried out in the presence of a cation exchange resin, in particular of Amberlite type as described in document CN101165038.

According to another particular aspect, the etherification or esterification reaction may be carried out enzymatically.

According to the present invention, the acid is generally used in a catalytic amount. In general, the amount of acid used is between 0.001 equivalent and 0.9 equivalent relative to the amount of vanillyl alcohol present in composition (C).

According to the present invention, the reaction may be carried out at a temperature between 10° C. and 100° C., preferably between 20° C. and 80° C., preferably at a temperature below or equal to 50° C., and more preferentially at a temperature between 25° C. and 40° C.

According to the present invention, the reaction is generally carried out at atmospheric pressure.

According to the present invention, at the end of step (i), a composition (C1) is obtained comprising natural vanillin and a compound of formula (I). According to the present invention, composition (C1) may also comprise at least one compound chosen from vanillic acid, vanillyl alcohol, acetovanillone, guaiacol and vinyl guaiacol.

Advantageously, the composition (C1) comprises between 0.1 ppm and 500 ppm of vanillyl alcohol, preferably the composition comprises less than 200 ppm of vanillyl alcohol, more preferentially less than 100 ppm and even more preferentially less than 50 ppm.

Advantageously, the weight ratio between vanillyl alcohol and vanillin in composition (C1) is less than or equal to 0.5, preferably less than or equal to 0.2, very preferentially less than or equal to 0.1 and even more preferentially less than or equal to 0.01.

According to one particular aspect of the present invention, step (i) also enables the formation of a compound of formula (III), according to the following formula, from vanillic acid present in composition (C):

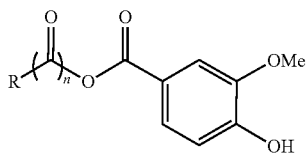

Formule (III)

wherein n is equal to 0 or 1, and R is chosen from a linear or branched, saturated or unsaturated alkyl group, optionally substituted with at least one hydroxyl, alkoxy or amine group, or a group of formula —(W—O)$_m$—X, wherein W is a linear or branched alkyl chain comprising from 1 to 4 carbon atoms and the average molecular weight of the —(W—O)$_m$— group is between 200 and 3000 g/mol and X is chosen from H and a unit of formula (IV)

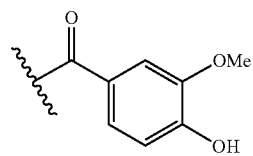

Formule (IV)

The formation of the compound of formula (III) is carried out in the presence of natural vanillin.

The formation of the compound of formula (III) may be simultaneous with the formation of the compound of formula (I).

According to one particular aspect, at the end of step (i), a composition (C2) is obtained comprising natural vanillin, a compound of formula (I) and/or a compound of formula (III). According to the present invention, composition (C2) may also comprise at least one compound chosen from vanillic acid, vanillyl alcohol, acetovanillone, guaiacol and vinyl guaiacol.

Advantageously, the composition (C2) comprises between 0.1 ppm and 500 ppm of vanillyl alcohol, preferably the composition comprises less than 200 ppm of vanillyl alcohol, more preferentially less than 100 ppm and even more preferentially less than 50 ppm. Composition (C2) comprises between 0.1 ppm and 500 ppm of vanillyl alcohol, preferably the composition comprises less than 200 ppm of vanillyl alcohol, more preferentially less than 100 ppm and even more preferentially less than 50 ppm.

Advantageously, the weight ratio between vanillyl alcohol and vanillin in composition (C2) is less than or equal to 0.5, preferably less than or equal to 0.2, very preferentially less than or equal to 0.1 and even more preferentially less than or equal to 0.01.

Advantageously, the weight ratio between vanillic acid and vanillin in composition (C2) is less than or equal to 0.5, preferably less than or equal to 0.2, very preferentially less than or equal to 0.1 and even more preferentially less than or equal to 0.01.

Step (ii):

According to the present invention, step (ii) is a step of recovering natural vanillin and/or of recovering a compound of formula (I), that are present in composition (C1) or (C2).

According to a first aspect, step (ii) enables the recovery of the natural vanillin. The natural vanillin obtained at the end of step (ii) is a purified natural vanillin. In one variant, the natural vanillin obtained at the end of step (ii) is a composition comprising purified natural vanillin.

According to the present invention, the natural vanillin obtained at the end of step (ii) comprises between 0.1 ppm and 500 ppm of vanillyl alcohol, preferably the composition comprises less than 200 ppm of vanillyl alcohol, more preferentially less than 100 ppm and even more preferentially less than 50 ppm.

According to the present invention, the natural vanillin obtained at the end of step (ii) comprises between 0 and 200 ppm of 4-((4-hydroxy-3-methoxybenzyl)oxy)-3-methoxybenzaldehyde or 4-hydroxy-3-(4-hydroxy-3-methoxybenzyl)-5-methoxybenzaldehyde. Preferably the content of 4-((4-hydroxy-3-methoxybenzyl)oxy)-3-methoxybenzaldehyde or 4-hydroxy-3-(4-hydroxy-3-methoxybenzyl)-5-methoxybenzaldehyde is less than or equal to 100 ppm, preferably less than or equal to 50 ppm and more preferentially less than or equal to 20 ppm. Preferably the content of 4-((4-hydroxy-3-methoxybenzyl)oxy)-3-methoxybenzaldehyde or 4-hydroxy-3-(4-hydroxy-3-methoxybenzyl)-5-methoxybenzaldehyde is greater than or equal to 0.01 ppm, and more preferentially greater than or equal to 0.1 ppm.

Advantageously, the treatment process according to the present invention also makes it possible to improve the overall yield of the treatment process compared with conventional purification methods.

According to the present invention, the process may comprise an additional step (iii) wherein the natural vanillin obtained at the end of step (ii) is shaped, preferably in the form of crystals, powder, beads or pearls.

According to the present invention, the natural vanillin titer at the end of step (ii) or (iii) is greater than or equal to 95%, preferably greater than or equal to 97%, very preferentially greater than or equal to 99%, even more preferentially greater than or equal to 99.5%. Very preferentially, the natural vanillin titer at the end of step (ii) or (iii) is greater than or equal to 99.95%.

According to the present invention, the natural vanillin at the end of step (ii) or (iii) is weakly colored. Preferably, the natural vanillin at the end of step (ii) or (iii) has a color of less than or equal to 400 Hazen, preferably of less than or equal to 200 Hazen, more preferentially of less than or equal to 100 Hazen, very preferentially of less than or equal to 50 Hazen and more preferentially still of less than or equal to 20 Hazen. The color is measured in a 10% by weight ethanolic solution. The color measurements are performed with a Konica Minolta CM-5 spectrophotometer using a cuvette with an optical path length of 10 mm.

Advantageously, the natural vanillin at the end of step (ii) or (iii) has organoleptic properties that are compliant, in particular in terms of visual appearance, texture, taste or fragrance. Advantageously, the composition according to the present invention does not exhibit false notes. Preferably, the organoleptic profile of the composition according to the present invention is at least equivalent to the organoleptic profile of the natural vanillin extracted from pods.

According to another aspect, step (ii) enables the recovery of the compound of formula (I).

According to the present invention, the content of natural vanillin in the compound of formula (I) is less than or equal to 200 ppm, preferably less than or equal to 100 ppm. According to the present invention, the content of natural vanillin in the compound of formula (I) is greater than or equal to 0.1 ppm.

According to another aspect, step (ii) enables the recovery of the natural vanillin and the compound of formula (I) is not recovered. The compound of formula (I) may be degraded during step (ii).

According to another aspect, step (ii) comprises the recovery of the natural vanillin and the recovery of the compound of formula (I). The steps for recovering the natural vanillin and the compound of formula (I) may be carried out simultaneously or successively in any order.

In particular, step (ii) enables the recovery of a compound of formula (I) in which n=0 and R is a butyl group.

According to the present invention, the purification yield of natural vanillin is greater than or equal to 75%, preferably greater than or equal to 80%, preferably greater than or equal to 90%, even more preferentially greater than or equal to 95%, and very preferentially greater than or equal to 99%. The purification yield of natural vanillin corresponds to the ratio of the amount of natural vanillin isolated at the end of step (ii) to the amount of natural vanillin in composition (C).

Step (ii) may be carried out by vacuum distillation, in particular in a falling film evaporator or a wiped film evaporator in order to prevent thermal degradation phenomena.

Step (ii) may in particular be carried out under the conditions described in document WO 2018/146210 or WO 2014/114590. In a variant, step (ii) may be carried out according to the conditions described in EP 2 791 098.

Preferably, when step (i) is carried out in the presence of an acid, the process according to the present invention may comprise an optional neutralization step, at the end of step (i) and before step (ii). In one embodiment, the neutralization step is not optional and/or may be carried out during step (ii). The neutralization may be carried out in the presence of a weak base or a strong base. Preferably, the neutralization may be carried out with NaOH, KOH, in solid form or in aqueous solution. Alternatively, the neutralization may be carried out in the presence of $NaHCO_3$, $KHCO_3$, $Na_2CO_3$, in solid form or in aqueous solution.

Finally, the present invention relates to a process for purifying a composition comprising natural vanillin and vanillyl alcohol by separating a compound of formula (I).

The present invention also relates to a process for preparing a compound of formula (I) in the presence of natural vanillin.

The natural vanillin capable of being obtained according to the process of the present invention is also a subject of the present invention.

The compound of formula (I) capable of being obtained according to the process of the present invention is also a subject of the present invention. To this end, the invention relates to a compound of formula (I) as described above in which n=0 and R=butyl and in which the compound of formula (I) is natural. Advantageously, such a compound is considered to be natural with regard to legislation, in particular in the United States. The compound of formula (I) as described above in which n=0 and R=butyl may be obtained according to step (i) defined above from a natural compound of formula ROH and natural vanillyl alcohol, R being butyl. At the end of step (i), a step (ii) as defined above may be carried out in order to recover and/or isolate the natural compound of formula (I) in which n=0 and R=butyl.

The term "natural compound" is understood to mean a compound corresponding to the definition provided by legislation, for example in the United States this means that the compound must be obtained by physical, enzymatic or microbiological processes and only from materials of plant or animal origin.

The invention also relates to a composition comprising a compound of formula (I) as described above in which n=0 and R=ethyl or butyl, the compound of formula (I) being a natural compound, the composition further comprising less than 200 ppm of 4-((4-hydroxy methoxybenzyl)oxy)-3-methoxybenzaldehyde and/or 4-hydroxy-3-(4-hydroxy methoxybenzyl)-5-methoxybenzaldehyde. For example, the composition comprises between 0 and 200 ppm of 4-((4-hydroxy-3-methoxybenzyl)oxy)-3-methoxybenzaldehyde or 4-hydroxy-3-(4-hydroxy-3-methoxybenzyl)-5-methoxybenzaldehyde. Preferably the content of 4-((4-hydroxy methoxybenzyl)oxy)-3-methoxybenzaldehyde or 4-hydroxy-3-(4-hydroxy-3-methoxybenzyl) methoxybenzaldehyde is less than or equal to 100 ppm, preferably less than or equal to 50 ppm and more preferentially less than or equal to 20 ppm. Preferably the content of 4-((4-hydroxy methoxybenzyl)oxy)-3-methoxybenzaldehyde or 4-hydroxy-3-(4-hydroxy-3-methoxybenzyl) methoxybenzaldehyde is greater than or equal to 0.01 ppm, and more preferentially greater than or equal to 0.1 ppm.

Finally, the present invention relates to the use of a natural vanillin composition as a flavoring in the human and animal nutrition field, in pharmacy, and as a fragrance in the cosmetics, perfumery and detergency industries.

The process according to the invention will be better understood on reading the following example which is a particular embodiment of the process. This example is given purely by way of illustration and cannot be interpreted as limiting the invention. Should the disclosure of patents, patent applications and publications cited herein by way of reference contradict the description of the present application to the extent that it risks rendering a term uncertain, the present description shall prevail.

Example

Materials

The ethanol, sulfuric acid, sodium hydroxide solution and also the solvents used for the analyses are from Merck and were used without prior purification. High performance liquid chromatography (HPLC) is carried out using an Agilent 1260 analytical chain with a C18 column.

A composition (C) comprising natural vanillin, vanillyl alcohol and a solvent 51 was obtained following the treatment of the aqueous phase resulting from the fermentation of ferulic acid by a microorganism. The culturing of the microorganism was carried out according to the conditions described in EP 0 885 968 and the solvent 51 corresponded to ethyl acetate. Composition (C) was analyzed by HPLC and the results are presented in table 1.

In a step (i) 349.5 g of composition (C), 21 g of ethanol (ROH) and 0.5 g of 96% $H_2SO_4$ were introduced into a reactor. The mixture was stirred for 1 hour at room temperature in order to form a compound of formula I with R=ethyl, n=0. A composition (C1) comprising said compound of formula I and natural vanillin was thus obtained and was analyzed by HPLC. The results are presented in table 1.

TABLE 1

|  | Composition C | Composition C1 |
|---|---|---|
| Vanillin (mmol) | 505 | 505 |
| Vnillyl alcohol (mmol) | 50.8 | 2.1 |
| Compound of formula I (mmol) | 0 | 37.4 |

Composition C1 also comprised solvent S1 and "heavy" impurities, i.e. impurities which have a relative volatility lower than that of natural vanillin under the pressure and temperature conditions under consideration. The identification of vanillin and vanillyl alcohol was carried out by comparison with commercial standards.

Thus, owing to the treatment process according to the invention, the vanillyl alcohol was selectively converted to ether. Indeed, no loss of vanillin was observed: the content in composition (C) was the same as the content in composition (C1) and only vanillyl alcohol was converted to ether, namely to vanillyl ethyl ether.

In a step (ii), the composition (C1) was concentrated by evaporating a portion of the solvent S1. A concentrated composition (C1) of approximately 270 g was thus obtained.

The concentrated C1 medium was brought to pH 7 with a sodium hydroxide solution. The mixture obtained was washed with water. The organic phase was then removed with a rotary evaporator and the residue obtained was purified in a wiped film evaporator in order to obtain natural vanillin with a titer greater than 99% and a coloration of 19 Hazen.

The invention claimed is:

1. A process for treating a composition (C) resulting from a process for producing natural vanillin, the vanillin comprising natural vanillin and vanillyl alcohol, said treatment process comprising:
   a step (i) of forming a composition (C1) comprising natural vanillin and a compound of formula (I) formed via an etherification or esterification reaction from said vanillyl alcohol present in composition (C):

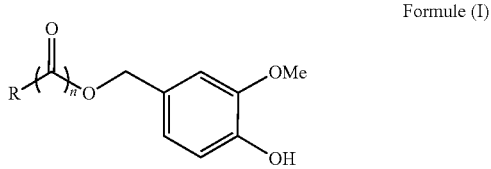

Formule (I)

wherein n is equal to 0 or 1, and R is chosen from a linear or branched, saturated or unsaturated alkyl group, optionally substituted with at least one hydroxyl, alkoxy or amine group, or R is a group of formula —(W—O)$_m$—X, wherein W is a linear or branched alkyl chain comprising from 1 to 4 carbon atoms and the average molecular weight of the —(W—O)$_m$—X group is between 200 and 3000 g/mol and X is chosen from H and a unit of formula (II), and

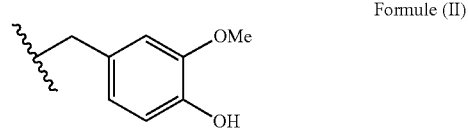

Formule (II)

a step (ii) of recovering said natural vanillin and/or a step of recovering said compound of formula (I) present in composition (C1).

2. The treatment process of claim 1, wherein step (i) is carried out in the presence of a compound chosen from the group consisting of ROH, RCOOH, and HO—(W—O)$_m$—H, wherein R is chosen from a linear or branched, saturated or unsaturated alkyl group, optionally substituted with at least one hydroxyl, alkoxy or amine group and W is a linear or branched alkyl chain comprising from 1 to 4 carbon atoms and the average molecular weight of the HO—(W—O)$_m$—H compound is between 200 and 3000 g/mol.

3. The treatment process of claim 1, wherein step (i) also enables the formation of a compound of formula (III), according to the following formula, from vanillic acid present in composition (C):

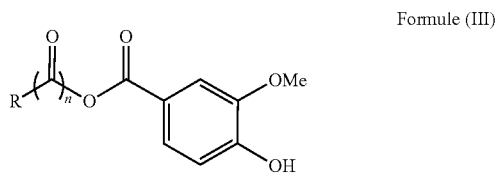

Formule (III)

wherein n is equal to 0 or 1, and R is chosen from a linear or branched, saturated or unsaturated alkyl group, optionally substituted with at least one hydroxyl, alkoxy or amine group, or a group of formula —(W—O)$_m$—X, wherein W is a linear or branched alkyl chain comprising from 1 to 4 carbon atoms and the average molecular weight of the —(W—O)$_m$—X group is between 200 and 3000 g/mol and X is chosen from H and a unit of formula (IV)

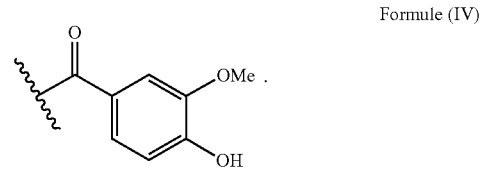

Formule (IV)

4. The treatment process of claim 1, wherein step (i) is an etherification reaction carried out in the presence of a compound of formula ROH, R being a butyl group, and wherein step (ii) is a step of recovering natural vanillin and of recovering a compound of formula (I) having n=0 and R being a butyl group.

5. The treatment process of claim 1, wherein the natural vanillin obtained at the end of step (ii) comprises less than 500 ppm of vanillyl alcohol.

6. The treatment process of claim 1, wherein the composition of the natural vanillin obtained at the end of step (ii) comprises less than 200 ppm of 4-((4-hydroxy-3-methoxybenzyl)oxy)-3-methoxybenzaldehyde or 4-hydroxy-3-(4-hydroxy-3-methoxybenzyl)-5-methoxybenzaldehyde.

7. The treatment process of claim 1, comprising an additional step (iii) wherein the natural vanillin obtained at the end of step (ii) is shaped in the form of crystals, beads, pearls, or powder.

8. The treatment process of claim 1, having a purification yield of greater than or equal to 90% relative to the amount of natural vanillin in composition (C).

9. The treatment process of claim 1, wherein the vanillin titer in the natural vanillin composition obtained at the end of step (ii) or (iii) is greater than or equal to 95%.

10. The treatment process of claim 1, wherein the natural vanillin obtained at the end of step (ii) or (iii) has a color of less than or equal to 400 Hazen.

11. A composition comprising:
a compound of formula (I)

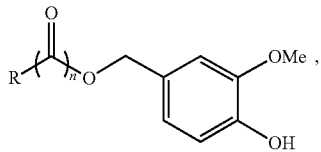

Formule (I)

wherein n is equal to 0 or 1, and R is chosen from a linear or branched, saturated or unsaturated alkyl group comprising from 1 to 10 carbon atoms, optionally substituted with at least one hydroxyl, alkoxy or amine group, or R is a group of formula $-(W-O)_m-X$, wherein W is a linear or branched alkyl chain comprising from 1 to 4 carbon atoms and the average molecular weight of the $-(W-O)_m-X$ group is between 200 and 3000 g/mol and X is chosen from H and a unit of formula (II); and 4-((4-hydroxy-3-methoxybenzyl)oxy)-3-methoxybenzaldehyde and/or 4-hydroxy-3-(4-hydroxy-3-methoxybenzyl)-5-methoxybenzaldehyde in an amount less than 200 ppm and greater than or equal to 0.01 ppm.

12. The composition of claim 11, wherein the compound of formula (I) is naturally produced.

13. The composition of claim 11, wherein the amount of 4-((4-hydroxy-3-methoxybenzyl)oxy)-3-methoxybenzaldehyde and/or 4-hydroxy-3-(4-hydroxy-3-methoxybenzyl)-5-methoxybenzaldehyde is greater than or equal to 0.1 ppm.

14. The composition of claim 11, wherein n=0 and R=ethyl or butyl.

15. The treatment process of claim 1, wherein the recovering of step (ii) further comprises separating the natural vanillin from the compound of formula (I).

16. The treatment process of claim 1, wherein the recovered natural vanillin has a purification yield of greater than or equal to 75%.

17. The treatment process of claim 1, wherein, when the compound of formula (I) is recovered, the compound of formula (I) has a natural vanillin content less than or equal to 200 ppm.

18. The treatment process of claim 1, wherein R is an alkyl group comprising from 1 to 10 carbon atoms.

* * * * *